United States Patent [19]

Gruber et al.

[11] 4,018,829

[45] Apr. 19, 1977

[54] METHOD FOR MAKING α-HYDROXY-ISOBUTYRAMIDE FROM ACETONE CYANOHYDRIN

[75] Inventors: Wilhelm Gruber, Darmstadt; Guenter Schroeder, Ober-Ramstadt, both of Germany

[73] Assignee: Rohm GmbH, Darmstadt, Germany

[22] Filed: June 2, 1976

[21] Appl. No.: 692,109

[30] Foreign Application Priority Data

June 18, 1975 Germany .................. 2527120

[52] U.S. Cl. .................. 260/561 B; 252/471
[51] Int. Cl.² .................. C07C 102/08
[58] Field of Search .......... 260/561 B; 252/471

[56] References Cited

UNITED STATES PATENTS

| | | | |
|---|---|---|---|
| 2,229,897 | 1/1941 | Migroichian | 260/561 B |
| 3,166,588 | 1/1965 | Johnson | 260/559 R |
| 3,403,178 | 9/1968 | Volker et al. | 260/561 B |
| 3,781,351 | 12/1973 | Fenton | 260/559 R |

Primary Examiner—Arthur P. Demers
Attorney, Agent, or Firm—Curtis, Morris & Safford

[57] ABSTRACT

In a method for making α-hydroxy-isobutyramide by the hydration of acetone cyanohydrin in the presence of manganese dioxide as a catalyst, the improvement wherein acetone is added to the reaction mixture.

4 Claims, No Drawings

METHOD FOR MAKING α-HYDROXY-ISOBUTYRAMIDE FROM ACETONE CYANOHYDRIN

The present invention relates to a method for making α-hydroxy-isobutyramide by the hydration of acetone cyanohydrin in the presence of manganese dioxide as a catalyst.

It is known that carboxylic acid amides can be prepared by the hydration of the corresponding nitriles, which process is favorably influenced by various catalysts. The conversion of nitriles into amides using a copper-containing catalyst is known from German patent publication DOS No. 2,001,903, wherein the catalyst comprises reduced copper oxide, reduced copper-chromium-oxide, reduced copper-molybdenum-oxide, or a mixture thereof.

A similar catalyst for the hydration of nitriles is described in U.S. Pat. No. 3,381,034: using metallic copper with copper-I-salts and/or copper-II-salts, acrylonitrile, for example, can be converted into acrylamide with good yield.

German patent publication DOS No. 2,036,126 teaches that Raney copper is also a good catalyst for the preparation of carboxylic acid amides by the addition of water to nitriles.

Finally, reference is made to German patent publication DOS No. 2,320,060 which has as its object a modification of known copper catalysts by magnesium silicate.

The use of the aforementioned copper-containing catalysts for the preparation of α-hydroxy-isobutyramide from acetone cyanohydrin leads to completely unsatisfactory results: However, manganese dioxide has proved to be an effective catalyst for this process.

The use of $MnO_2$ as a catalyst in the preparation of carboxylic acid amides from the corresponding nitriles, in general, is taught in German Pat. No. 1,593,320. In German patent-of-addition No. 2,131,813, in which an aqueous solution or emulsion of the carboxylic acid nitrile to be hydrated is led through an $MnO_2$ bed, the preparation of α-hydroxy-isobutyramide from acetone cyanohydrin is described by way of example. It is mentioned in the aforementioned German Pat. No. 1,593,320 that a manganese dioxide which is practically neutral is advantageously used as a catalyst, i.e. a material which, in the form of a slurry of one gram in 10 grams of water, has a pH value of 6.0 to 8.0. By repeating the Examples given in this patent, and also those given in the aforementioned patent-of-addition, one skilled in the art will find that the preparation of the catalyst requires a particular procedure which, however, does not lead, from batch to batch, to the production of catalysts having the same efficacy. A corresponding variation in the yields obtained with different catalysts must, according to the experience of the applicants, be accepted as a consequence. The improvement of the known process which is the subject of the present invention leads not only to an absolute increase in conversion and/or yield, but also to better uniformity in the course of the reaction when using differently-prepared catalysts.

It has been found that the aforementioned improvements in the known process are achieved if the hydration is carried out either in acetone or in the presence of acetone.

In German Pat. No. 1,593,320 mentioned several times above, the hydration of a nitrile in a liquid organic solvent is described as a preferred embodiment, wherein such solvents are chosen which permit working at elevated temperatures. Suitable solvents given as examples are dioxane (b.p. = 106° C.), chloroform (b.p. = 61° C.), benzene (b.p. = 80° C.), toluene (b.p. = 111° C.), pyridine (b.p. = 116° C.), β-picoline (b.p. = 144° C.) and tert.-amyl alcohol (b.p. = 102° C.).

According to German Pat. No. 2,131,813, the hydration of acetone cyanohydrin to α-hydroxy-isobutyramide at 25° C. is described. With a contact time of 2.67 hours, a conversion to the aforementioned amide of 60 percent is achieved.

If the hydration according to the present invention is carried out at temperatures between 50° and 90° C., either in an aqueous medium or in a methanolic medium or in acetone, the yields are raised, even with a reaction time of only one hour, to greater than 90 percent of theory.

It is noteworthy that when working in the aqueous medium, even an addition of 10 percent by weight of acetone, calculated on the acetone cyanohydrin (i.e. about 0.15 mol of acetone/mol of acetone cyanohydrin), the reaction can be carried out with a conversion of 100 percent and a yield of 93 percent of theory (cf. Example 7).

For the effects which are verified numerically below, no certain explanation can yet be given. The suggestion which first offers itself, that by the addition of acetone or by carrying out the hydration in acetone, the decomposition equilibrium of acetone cyanohydrin is displaced in favor of the stability of this product, is not satisfactory. The dissociation of acetone cyanohydrin requires an acid or basic environment, whereas in the neutral region required for carrying out the process according to German Pat. No. 1,593,320 dissociation occurs only to a negligible extent. Further, it cannot be assumed that the postulated displacement of equilibrium offered as an explanation of the effects achieved according to the present invention would be affected by such a small amount of acetone such as the already-mentioned amount of 0.15 mol of acetone/mol of acetone cyanohydrin as to lead to increases in yield of over 10 percent. (cf. comparison Examples 2 and 7).

It has already been mentioned that the efficacy of the manganese dioxide catalyst is dependent on the manner in which it is prepared and that it has not heretofore been possible to prepare this catalyst to have a consistent behavior, i.e. a consistent activity. German Pat. No. 1,593,320 describes the preparation of an effective $MnO_2$ catalyst by the reaction of equivalent amounts of manganese sulfate with potassium permanganate in the presence of a small excess of sodium hydroxide at 80° C.

$MnO_2$ is known in various modifications, as is extensively discussed in the "Zeitschrift fuer anorganische und allgemeine Chemie" 309, 1 – 36, 121 – 150 (1961). Badly crystallized products, the x-ray patterns of which show only a few more or less diffuse[+] diffraction reflections[++], are designated as δ-$MnO_2$. These products are primarily produced by the reaction of heptavalent manganese compounds in the neutral to alkaline region at 20° to 100° C.

[+] but relatively intense
[++] in the Debye patternat θ = 8,2°

It has been shown that the members of the δ MnO$_2$ class have a particularly high activity as catalysts in the hydration of acetone cyanohydrin.

Manganese dioxides of this particularly effective modification[+] have been used in the following Examples. In the following Examples, given by way of clarification, the method of the present invention is carried out in an aqueous medium with the addition of various amounts of acetone (Compilation 1), in a methanolic medium with the addition of about 1.5 mols of acetone/mol of acetone cyanohydrin (Compilation 2), and in acetone (Compilation 3). For the reaction in methanol and in acetone, the use of an amount of water necessary for the hydration of the acetone cyanohydrin is naturally required. In the Examples under discussion, water in about 100 percent excess of that theoretically necessary was used.

[+] Zeitschrift fur anorganische und allgemeine Chemie 309, 1–36, 121 – 150; German Pat. No. 1 593 320

The tests are now described more in detail.

EXAMPLE 1

Hydration in an Aqueous Medium

A mixture of 10 g of acetone cyanohydrin, 40 g of water, and 20 g of MnO$_2$ is warmed, with or without the addition of acetone, with stirring, to the temperatures indicated in the following compilation (50° C., 60° C., or 90° C.). The conversion is determined at periodic intervals by hydrocyanic acid titration according to Liebig.

After the times indicated in the individual tests, the reaction was interrupted, the catalyst was filtered off after cooling, and the α-hydroxy-isobutyramide which remained as a residue in a rotary evaporator after distilling off the volatile residues was isolated as a solid substance. The results of the comparison tests involving no addition of acetone and the tests carried out according to the present invention are given in the following Compilation.

COMPILATION 1

| Test No. | Temp. (° C.) | Acetone Addition (g) | Conversion (Percent) | Hours | Yield (percent of theory) |
|---|---|---|---|---|---|
| 1 | 50 | — | 96.6 | 3 | 86 |
| 2 | 60 | — | 98.3 | 3 | 80 |
| 3 | 90 | — | 99.2 | 1 | 83 |
| 4 | 60 | 10 | 99.0 | 1 | 95 |
| 5 | 60 | 5 | 100 | 3 | 93 |
| 6 | 60 | 3 | 99.1 | 3 | 93 |
| 7 | 60 | 1 | 100 | 3 | 93 |

EXAMPLE 2

Hydration in a Methanolic Medium

The performance of the tests corresponded with the tests described in Example 1 but with the added measure that 10 g of acetone cyanohydrin were diluted with 40 g of methanol and 4.4 g. of water. As the catalyst, 20 g of MnO$_2$ were added to the batch. The hydration was carried out both without acetone and, in the other cases, with an acetone addition (10 g). The results are to be found in the following Compilation.

COMPILATION 2

| Test No. | Temp. (° C.) | Acetone Addition (g) | Conversion (Percent) | Hours | Yield (percent of theory) |
|---|---|---|---|---|---|
| 8 | 60 | — | 90.4 | 1 | 69 |
| 9 | 60 | — | 92.9 | 1 | 85 |
| 10 | 60 | 10 | 92.5 | 1 | 91 |
| 11 | 60 | 10 | 93.5 | 1 | 91 |

A comparison of tests 8 and 9, on the one hand, and of 10 and 11, on the other hand, confirms the earlier statement that the use of acetone according to the present invention increases the uniformity of the course of the reaction when using catalysts from different batches. In tests 8 and 10, pyrolusite from one preparatory batch was used, and in Examples 9 and 11 a manganese dioxide from a different preparatory batch was used. The yields in the tests carried out without the addition of acetone (8 and 9) show a remarkable variation; in one case a yield of 69 percent was obtained and in the other case a yield of 85 percent was obtained.

In contrast thereto, the manganese dioxides obtained from two different batches, but used with the addition of acetone, gave yields in good agreement of 91 percent.

EXAMPLE 3

Reaction in Acetone

The general test conditions were those employed in Examples 1 and 2 but with the differences that the hydration was carried out in 40 g of acetone to which 4.4 g of water were added. The reaction mixture was kept for 3 hours at the boiling temperature of acetone (56° C.).

COMPILATION 3

| Test No. | Temp. (° C.) | Acetone Addition (g) | Conversion (Percent) | Hours | Yield (percent of theory) |
|---|---|---|---|---|---|
| 12 | 56 | 40 | 92.7 | 3 | 90 |

As shown in these Examples, the process can be carried out discontinuously, and advantageously at temperatures between 60° and 90° C. However, the reactin mixture can also be introduced continuously into one or more reactors and after leaving the reactor can be worked up in an analogous fashion.

What is claimed is:

1. In a method for makin α-hydroxy-isobutyramide by the hydration of acetone cyanohydrin in the presence of manganese dioxide as a catalyst, the improvement wherein acetone is added to the reaction mixture.
2. A method as in claim 1 wherein the amount of acetone used is greater than 0.1 mol/mol of acetone cyanohydrin.
3. A method as in claim 1 wherein said manganese dioxide is of the δ-modification.
4. A method as in claim 1 wherein the reaction is carried out in an aqueous medium at a temperature between 60° and 90° C.

* * * * *